United States Patent [19]

Bottka et al.

[11] Patent Number: 4,953,983
[45] Date of Patent: Sep. 4, 1990

[54] NON-DESTRUCTIVELY MEASURING LOCAL CARRIER CONCENTRATION AND GAP ENERGY IN A SEMICONDUCTOR

[76] Inventors: Nicholas Bottka, 5642 Mt. Burnside, Burke, Va. 22015; D. Kurt Gaskill, 3187 Lawson Hill Pl., Alexandria, Va. 22310; Robert Glosser, 2909 Deep Valley Trail, Plano, Tex. 75075

[21] Appl. No.: 172,921

[22] Filed: Mar. 25, 1988

[51] Int. Cl.$^5$ ................... G01N 21/55; G01N 21/84
[52] U.S. Cl. ............................. 356/445; 356/30; 356/432
[58] Field of Search ............ 356/30, 432 T, 445, 356/447, 448

[56] References Cited

U.S. PATENT DOCUMENTS 4,211,488  7/1980  Kleinknecht ................... 356/432
4,652,757  3/1987  Carver ....................... 250/360.1

OTHER PUBLICATIONS

Glosser et al., "Comparative Responses of Electroreflectance and Photoreflectance in GaAs", SPIE Conference, Bay Point, FL. Mar. 27, 1989.
Glembocki et al., "Photoreflectance Characterization of GaAs/AlGaAs Thin Films, Heterojunctions, and Multiple Quantum Well Structures", SPIE, vol. 524, (1985), pp. 86–94.
Glembocki et al., "Photoreflectance Characterization of Interband Transitions in GaAs/AlGaAs Multiple Quantum Wells and Modulation–Doped Heterojunctions", Appl. Phys. Lett. 46(10), May 15, 1985, pp. 970–972.

*Primary Examiner*—Richard A. Rosenberger

[57] ABSTRACT

An apparatus and method for non-destructive measuring of local carrier concentration and bandgap in a semiconductor such as gallium arsenide or gallium aluminum arsenide. A high energy source of photons, e.g. a laser, photo injects carriers on the surface of the semiconductor causing a change in the semiconductor's surface photo reflectance. The fractional change in photo reflectance is measured for a plurality of the photon energies sufficient to identify several Franz-Keldysh peaks, and the photon energies corresponding to these peaks. This information is used to infer the local electric field strength and carrier concentration of the semiconductor as well as semiconductor's bandgap. By noting variations in these parameters throughout the bulk semiconductor, one can identify fatal fabrication flaws in the semiconductor crystal before time and money is expended to fabricate complicated semiconductor architectures in the crystal.

14 Claims, 3 Drawing Sheets

NON-DESTRUCTIVELY MEASURING LOCAL CARRIER CONCENTRATION AND GAP ENERGY IN A SEMICONDUCTOR

BACKGROUND OF THE INVENTION

The invention pertains to the non-destructive testing of semiconductor material parameters, and most especially to flaw testing of semiconductors by measuring local carrier concentration and gap energy.

In the manufacture of semiconductor devices, such as field effect transistors, one typically begins with a large substrate wafer of semiconductor material, and forms a large number of semiconductor devices in the wafer, finally cutting the wafer into individual devices and packaging them. These manufacturing steps are time consuming and expensive. It is thus of fundamental importance to the manufacturing process of such semiconductor devices that the original wafer of semiconductor material be essentially free of fatal material flaws. Such flaws generally manifest themselves by significant local deviation from desired carrier concentration. Present techniques to test carrier concentration are generally destructive, that is, consume the material tested, rendering it unfit for further use. For this reason, present engineering practice is to sacrifice a very small portion of large semiconductor substrate wafers in the hopes that the small area tested shares the same characteristics of the areas untested, often a very bad and costly assumption. These problems are especially important to the fabrication of gallium arsenide and gallium aluminum arsenide, whose technology is less mature than, for example, that of silicon, and in which one would expect a greater likelihood of undetected fabrication flaws. Thus the semiconductor industry has a plain need for a quick, simple, and inexpensive non-destructive method for measuring local carrier concentration in semiconductors, most especially gallium arsenide or gallium aluminum arsenide.

Additionally, the gap energy of a semiconductor is an important material parameter, the measuring of which is important both in industry and in research. Any technique for quickly, easily, and non-destructively measuring gap energy would be a welcome addition to the art.

SUMMARY OF THE INVENTION

Accordingly, it is an object of this invention to enable one to locate fatal flaws in semiconductors by non-destructive techniques.

Another object of this invention is to enable one to non-destructively test for local carrier concentration in semiconductors.

Another object of this invention is to enable one to non-destructively measure semiconductor bandgap.

Another object of this invention is to do the foregoing quickly, simply, inexpensively, and reliably.

Another object of this invention is to enable one to do the foregoing on wafers of semiconductor substrates before fabrication in these substrates of complicated semiconductor architectures.

Another object of this invention is to do the foregoing by photo reflective techniques, as is explained below.

These, and other objects that shall become apparent hereinafter, are secured by apparatus and methods founded on a knowledge of photo reflectance in general, and the Franz-Keldysh relationship in particular.

For Gallium Arsenide, Aluminum Gallium Arsenide, or any material having a valence-conduction bandgap $E_g$ whose conduction properties are set, or at least dominated, by valence-conduction band transitions at critical points in reciprocal space, and on which photons are incident (such as that of a laser) with energy greater than the critical point transition energy $E_g$, then the photo-induced fractional change in the material's reflectance $(\Delta R)/R$ is given by the spectral line shape equation, i.e.:

$$\frac{\Delta R}{R} \alpha \cos\left[\frac{2}{3}\left(\frac{\zeta\omega - E_g}{\zeta\Omega}\right)^{3/2}\right]$$

where $\Delta R$ is the change in material reflectance $R$ responsive to bombarding photons of energy $\zeta\Omega$, d is the dimensionality of the material's critical point transition, a material constant, $\zeta$ is Planck's constant divided by $2\pi$, and $\omega$ is $2\pi$ times the frequency of the light inducing $\Delta R$. This relationship is in the form of a sinusoid, but oscillating in photon energy $(\zeta\omega)$ rather than in time. As such, the equation has a number of peaks, sometimes referred to as Franz-Keldysh peaks, i.e., for the nth such peak, $n = 0, 1, 2, 3 \ldots \infty$:

$$n\pi = \frac{2}{3}\left[\frac{\zeta\omega - E_g}{\zeta\Omega}\right]^{3/2}$$

Conventional quantum electromagnetic field theory teaches that the characteristic energy $\zeta\Omega$, of a carrier particle in a local electric field is:

$$\zeta\Omega = \left[\frac{e^2\zeta^2 F^2}{8\mu}\right]^{1/3}$$

where $e$ = electron charge, $u$ = the reduced mass of a carrier particle (electron or hole), and $F$ = the local electric field strength. The Schottky equation relates electric field strength $F$ to local carrier concentration, i.e.:

$$F = \frac{2e(N_D + N_A)\left(V_B - V_P - \frac{kT}{e}\right)}{k\epsilon_o}$$

where $V_B$ and $V_P$ are the respective built-in and photo-induced voltages in the semiconductor, k is Boltzmann constant, T is absolute temperature of the semiconductor, $\epsilon_o$ is the permittivity of free space, K is the dielectric constant of the semiconductor, and $(N_D + N_A)$ is the sum of the respective ionized donor and acceptor carrier concentrations, the desired quantity. Accordingly, if one can measure the quantity $\zeta\Omega$, one can use these relationships to infer local carrier concentration. Because the architecture of most semi-conductor devices resides near the surface of the device's semiconductor substrate wafer, inspection of material parameters critical to semiconductor architecture can be done by photo reflective techniques, techniques that are inherently nondestructive.

This is achieved by providing apparatus and methods that photo reflectively determine several Franz-Keldysh peaks for a localized portion of a semiconductor, and use the equations above to infer the carrier concentration at that local portion of the semiconductor. The apparatus illuminates the local portion of the semiconductor with two light beams, each of a preselected single wavelength, one operating to excite the semiconductor by photoinjecting carriers, the other corresponding to $\zeta\Omega$. The apparatus measures the fractional change in reflectance of the light of energy $\zeta\Omega$ responsive to the excitation light, records this fractional change, for various values of $\zeta\Omega$ to generate several Franz-Keldysh peaks, identifies the photon energies corresponding to these peaks, and uses this information to infer the local carrier concentration in the manner discussed above. Besides merely measuring the local carrier concentration, one can test the measured concentration against a standard norm, and annunciate any unacceptably large deviation from this norm so that a process operator can take appropriate action, for example, discarding the entire substrate as unsatisfactory. Moreover the measuring of $\zeta\Omega$, an important intermediate calculation leading towards carrier concentration, is especially well suited to graphical technique. For example taking the cosine terms in the spectral-line shape relationship:

$$n\pi = \frac{2}{3}\left[\frac{\zeta\omega - E_g}{\zeta\Omega}\right]^{3/2} - \frac{\pi(d-1)}{4}$$

one can rearrange it to the form:

$$(\zeta\omega)_n = \zeta\Omega\left\{\frac{3\pi}{2}\left[n + \frac{d-1}{4}\right]\right\}^{2/3} + E_g$$

For a direct gap material such as gallium arsenide, d=3, i.e.

$$(\zeta\omega)_n = \zeta\Omega\left\{\frac{3\pi}{2}(n + \tfrac{1}{2})\right\}^{2/3} + E_g$$

Defining a variable $\chi_m$ such that:

$$X_n = \left\{\frac{3\pi}{2}\left(n + \frac{d-1}{4}\right)\right\}^{2/3}$$

Then the expression for $(\zeta\omega)_m$ becomes:

$$(\zeta\omega)_n = (\zeta\Omega)\chi_n + E_g$$

which is in the form of a straight line plot of $(\zeta\omega)_n$ versus $\chi_n$, with a slope $(\zeta\Omega)$ and intercept of the $(\zeta\omega)_n$ axis of $E_g$. By measuring the energies $(\zeta\omega)_n$ which correspond to several Franz-Keldysh peaks, and identifying n for those peaks one has identified, one can make such a linear plot, and graphically identify $E_g$ and $\omega\Omega$, the latter enabling one to calculate the local field F, and carrier concentration $(N_A + N_D)$, according to the above equations.

The invention is more fully understood from the following detailed description, it being recognized however, that the invention is capable of extended application and is not confined to the precise details of the disclosure. Changes and modifications can be made that do not affect the spirit of the invention as set forth in the appended claims, nor exceed the scope thereof. Accordingly, the invention is now described with particular reference to the accompanying drawings, wherein:

DETAILED DESCRIPTION OF THE INVENTION

Figure 1:
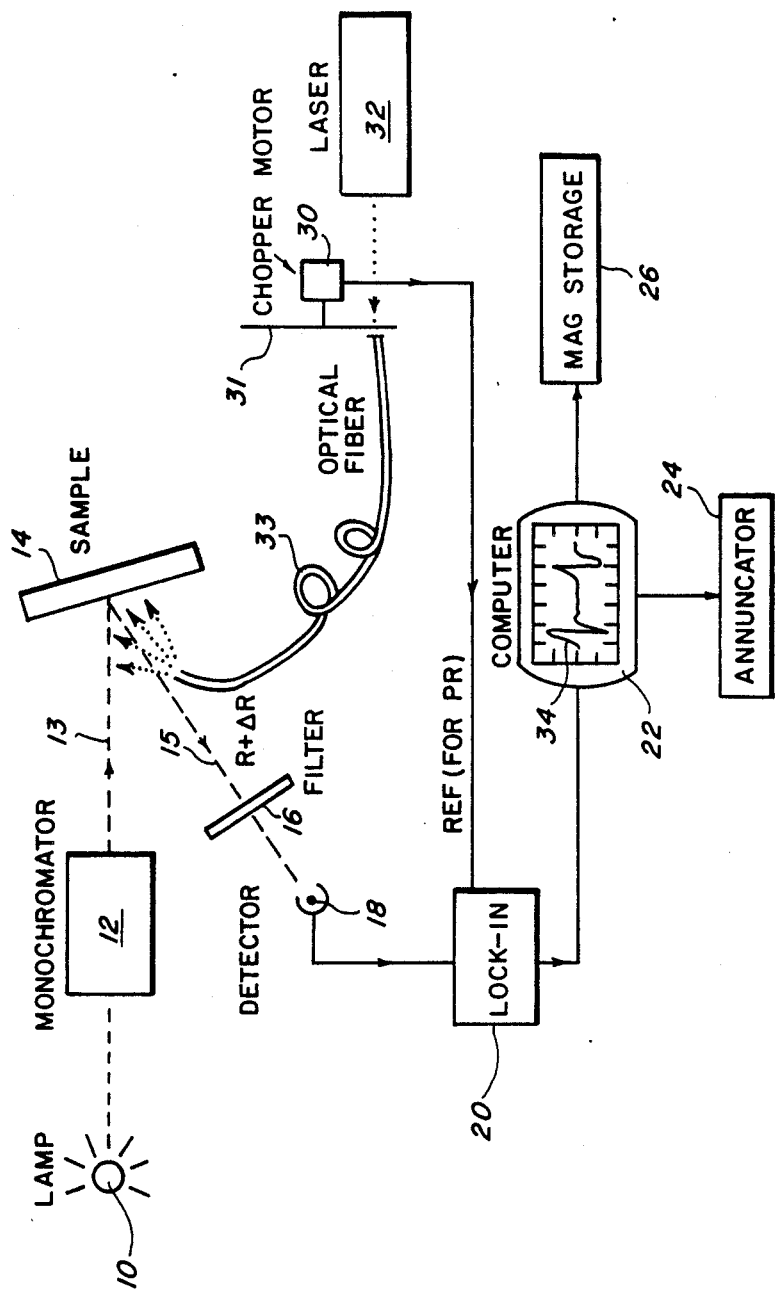
FIG. 1 is a schematic diagram of an apparatus for practicing the invention.

With reference to the drawing figures, wherein like references indicate like structure or information throughout the several figures, FIG. 1 illustrates schematically a system for practice of the invention. Monochromator 12 filters light from lamp 10, producing a monochromatic beam of light 13 directed at semiconductor sample 14. Laser 32, whose output is also, of course, monochromatic, is arranged so that the lasing light is directed via fiber optic coupler 33 to the same portion of semiconductor 14 that is illuminated by lamp 10 and monochromator 12. Monochromatic light 13 is reflected as shown at 15 and directed at filter 16, which filters light from laser 32. The magnitude of reflected beam 15 is detected by photo detector 18. Monochromator 12, filter 16 and detector 18 can be of any conventional type well known to those skilled in the optics art. That coupler 33 be fiber optic is not critical; any transmission means will do so long as light of laser 32 is directed to sample 14 as herein described. A screen 31 opaque to the output of laser 32 is movably disposed to either block or pass the output of laser 32 to sample 14 responsive to the movement of chopper motor 30. In this fashion, chopper motor 30 can be moved at a regular frequency to cause output of laser 32 to pulse onto sample 14 at a predetermined chopping rate. A lock-in amplifier 20, also of conventional type, is keyed to the frequency of chopper motor 30 so as to pass optical signals from detector 18 only if these signals are in phase with the frequency of chopper motor 30. Process computer 22 responds to the output of lock-in amplifier 20 to translate signals received at 18, 20 into usable form in a manner that will be described below, and off loads this data into recorder, or storage area 26. Storage 26 can be of any conventional type, and is preferably magnetic disk storage.

In operation, with laser 32 turned off, the system can be used to measure simple reflectance as a function of monochromatic wavelength. Lamp 10 and monochromator 12 generate a monochromatic light 13 incident on a portion of sample 14. Sample 14 reflects part of light 13 and absorbs part. The reflected portion 15 is incident upon detector 18 which, in measuring the intensity of light 15, also inferentially measures the fraction absorbed by sample 14, and thus the reflectance of sample 14 when unperturbed by light from laser 32, providing a baseline against which to make later measurements. With laser 32 turned on, optical transmitter 33 directs the output of laser 32 onto the same portion of sample 14 also illuminated by lamp 10 and monochromator 12. The photons output by laser 32 are of an energy sufficient to cause electron-hole generation in sample 14, in effect photo injecting carriers into sample 14 and altering sample 14's local carrier concentration. This in turn changes sample 14's reflectance by an amount ΔR whose magnitude is detected by detector 18. Lock-in amplifier 20, being keyed to chopper motor 30, and thus to the rate at which sample 14 is pulsed by laser 32, passes signals from photo detector 18 during the time that laser 32 is pulsing sample 14, enabling computer 22 to record in its memory the change in reflectance induced by the pulsing of laser 32. Computer 22 is preprogrammed in a conventional manner to automatically calculate ΔR/R, and stores this in storage area 26. The photo-energy $\zeta\omega$ of the monochromator output can be selectively varied, and the foregoing procedures repeated to generate a database relating the fractional change in reflectivity ΔR/R to photon energy $\zeta\omega$ which is then stored in magnetic storage area 26. Computer 22, which can be any commercially available process computer dedicated in the manner described herein, in its simplest form merely reads these data onto magnetic storage 26 for later analysis (e.g. by the graphical techniques, discussed below). The data input into computer 22 will vary in time as shown by curve 34, the spikes of curve 34 corresponding to changes of reflectance responsive to pulses from laser 32, and computer 22 is programmed to calculate ΔR/R using the above-mentioned reflectance baseline In this manner, computer 22 generates a database relating to ΔR to laser photon energy $\zeta\omega$.

Figure 2:
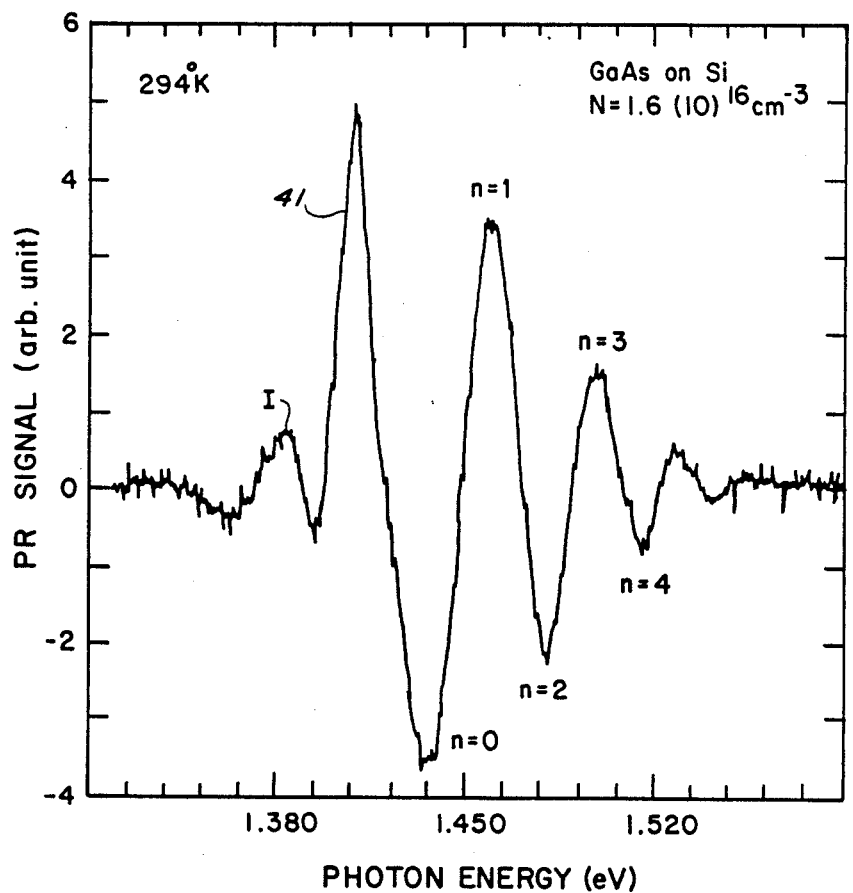
FIG. 2 is a graph, illustrating reflectance of a gallium arsenide sample as a function of photon energy $\zeta\omega$. This plot illustrates the Franz-Keldysh oscillations.

Additionally, and preferably, computer 22 can also be programmed to examine this database for Franz-Keldysh peaks, and to identify the peak indices n and monochromator output energies $(\zeta\omega)_m$ corresponding to these peaks. Computer 22 can also be programmed with the equations listed above to use these peak energies and indices n to calculate on line the carrier concentration of the portion of semiconductor 14 under test. Should computer 22 determine that the carrier concentration varies by a predetermined amount from optimal, computer 22 can cause an annunciator 24, of any conventional type, to indicate this variance. A graphical representation of ΔR/R as a function of $(\Delta\omega)_n$ is shown in FIG. 2, which displays data taken on a wafer of gallium arsenide at 294° K. The wafer was grown epitaxially on a silicon substrate, and doped to an electron carrier density of $1.6 \times 10^{16}$ per cubic centimeter.

Five Franz-Keldysh peaks were identified and labeled with their corresponding peak indices n=0, 1, 2, 3 and 4. Also seen is the leading edge of the curve 41, which is interrupted by the oscillation for n=0 at about 1.40 ev. Also seen is a pseudo-peak "I" at about 1.38 ev, which is unrelated to Franz-Keldysh phenomena, and is believed to have resulted from impurities in the gallium arsenide sample.

Figure 3:
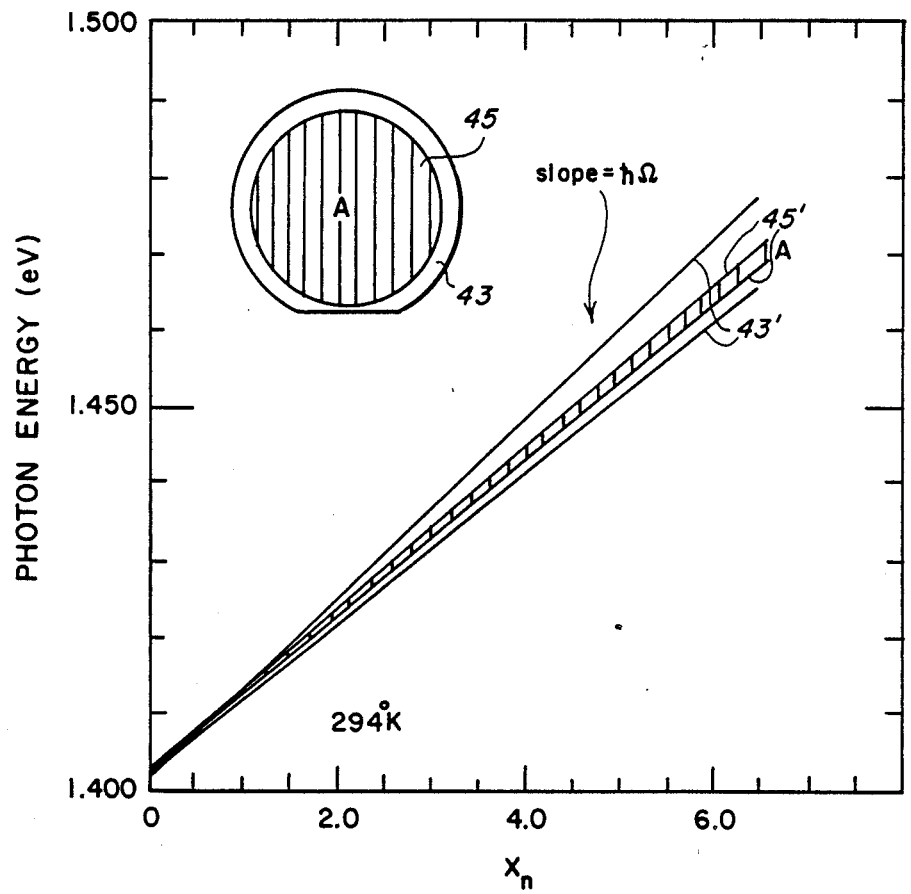
FIG. 3 is a graph showing the graphical method described above for determining $\zeta\Omega$ and $E_g$.

With particular reference to FIG. 3, the graphical technique for determining carrier concentration and gap energy is illustrated. FIG. 3 is based on data taken at various locations on the sample on which the data of FIG. 2 was taken, and the slight deviation in line slope indicates local deviation in field strength F, which causes local carrier concentration $(N_A + N_D)$ to vary. In particular, the greatest deviation occurred at locations about periphery 43 of the sample (marked "A"), whereas more central portions 45 of sample A showed far less local deviation. The greatest and least slopes measured at the periphery is shown by lines 43', and within the periphery by 45'. All these lines converge near the "photon energy" $(\zeta\omega)$ axis at 1.404 ev, the sample's bandgap $E_g$.

The invention is shown and described herein in what is considered to be the most practical and preferred embodiments. It is recognized, however, that departures may be made within the scope of the invention and that obvious modifications will occur to a person skilled in the art. Accordingly, the scope of the invention is to be determined solely by reference to the appended claims.

What is claimed and desired to be secured by Letters Patent of the United States is:

1. A method for measuring local carrier concentration in a preselected portion of a semiconductor, said method comprising steps for:
    illuminating said preselected portion of said semiconductor with a substantially monochromatic light of a preselected photon energy;
    measuring change in photo reflectance of said portion of said semiconductor responsive to said illuminating by said light of said preselected photon energy;
    recording said change in photo reflectance;
    repeating said steps for illuminating, measuring, and recording, each said repeating of said steps for illuminating, measuring, and recording being done with a substantially monochromatic light of a different preselected photon energy;
    said repeating of said steps being done a sufficient number of times to permit location of at least two Franz-Keldysh peaks, and identification of the respective photon energies and peak indices n corresponding to each of said at least two Franz-Keldysh peaks;
    recording each of said respective photon energies and peak indices n;
    using said each of said respective photon energies and peak indices n to calculate said local carrier concentration.

2. The method of claim 1 wherein said method comprises a step for determining if said local carrier concentration varies by a preselected amount from a preselected value.

3. The method of claim 2 wherein said method comprises a step for annunciating said carrier concentration varying by said preselected amount from said preselected value.

4. The method of claim 1, wherein said step for using said at least two Franz-Keldysh peaks comprises steps for;
    calculating a variable $$X_n = \left\{ \frac{3}{2} \pi \left[ n + \left( \frac{d-1}{4} \right) \right] \right\}^{2/3},$$

where d is the dimensionality of the critical points of transition of said semiconductor;
    making a linear plot of said indices n versus said respective photon energies;
    measuring the slope of said linear plot;
    using said slope to calculate the local electric field at said preselected portion of said semiconductor; and
    using said electric field to calculate said local carrier concentration.

5. An apparatus for measuring local carrier concentration in a preselected portion of a semiconductor, said apparatus comprising:

means for illuminating said preselected portion of said semiconductor with a substantially monochromatic light of a preselected photon energy;

means for measuring change in photo reflectance of said portion of said semiconductor responsive to said illuminating of said light of said preselected photon energy;

means for recording said change in photo reflectance;

wherein said means for illuminating, means for measuring, and means for recording constitute means for generating a database of change of photo reflectance for a plurality of said photon energies sufficient to permit location of at least two Franz-Keldysh peaks, and identifying the respective photon energies and peak indices n corresponding to each of said at least two Franz-Keldysh peaks;

wherein said means for recording is effective to record each of said respective photon energies and peak indices n;

and wherein said apparatus further comprises means for using each of said respective photon energies and indices n to calculate said local carrier concentration.

6. The apparatus in claim 5 wherein said apparatus comprises a means for determining if said local carrier concentration varies by a preselected amount from a preselected value.

7. The apparatus in claim 6 wherein said apparatus comprises means for annunciating said carrier concentration varying by preselected amount from said preselected value.

8. The apparatus in claim 5 wherein said means for using comprises means for:

calculating a variable $$x_n = \left\{ \frac{3}{2} \pi \left[ n + \left( \frac{d-1}{4} \right) \right] \right\}^{2/3}$$

where d is the dimensionality of the critical point of transition of said semiconductor;

making a linear plot of said $\chi_n$ versus said respective photon energies;

measuring the slope of said linear plot;

using said slope to calculate said local carrier concentration.

9. A method for measuring the bandgap of a semiconductor, said method comprising steps for:

illuminating said semiconductor with a substantially monochromatic light of a preselected photon energy;

measuring change in photo reflectance of said semiconductor responsive to said illuminating by said light of said preselected photon energy;

recording said change in photo reflectance;

repeating said steps for illuminating, measuring, and recording, each said repeating of said steps for illuminating, measuring, and recording being done with a substantially monochromatic light of a different preselected photon energy;

said repeating of said steps being done a sufficient number of times to permit location of the respective photon energies and peak indices n corresponding to at least two Franz-Keldysh peaks;

recording the photon energy and peak index n corresponding to each of said at least two Franz-Keldysh peaks;

using said respective photon energies and indices n to calculate said bandgap of said semiconductor.

10. The method of claim 9, wherein said method comprises a step for annunciating the magnitude of said bandgap.

11. The method of claim 10 wherein said step for using said respective photon energies and indices n comprises steps for:

calculating a variable $$x_n = \left[ \frac{3}{2} \pi \left( n + \frac{d-1}{4} \right) \right]^{2/3},$$

where d is the dimensionality of the critical point of transition of said semiconductor;

making a linear plot of said $\chi_m$ versus said respective photon energies; and identifying said bandgap by identifying the intercept of the axis of said linear plot corresponding to said respective photon energies.

12. An apparatus for measuring the bandgap of a semiconductor, said apparatus comprising:

means for illuminating said semiconductor with a substantially monochromatic light of a preselected photon energy;

means for measuring change in photo reflectance of said semiconductor responsive to said illuminating by said light of said preselected photon energy;

means for recording said change in photo reflectance wherein said means for illuminating, means for measuring, and means for recording constitute means for generating a database of change of photo reflectance for a plurality of said photon energies sufficient to permit location of at least two Franz-Keldysh peaks, and identification of the respective photon energies and peak indices n corresponding to each of said at least two Franz-Keldysh peaks; said apparatus further comprising:

means for recording said respective photon energies and peak indices corresponding to each of said at least two Franz-Keldysh peaks; and means for using said respective photon energies and peak indices to calculate said bandgap of said semiconductor.

13. The apparatus of claim 12, further comprising means for annunciating the magnitude of said bandgap.

14. The apparatus of claim 12, wherein said means for using comprises means for:

calculating a variable $$x_n = \left\{ \frac{3\pi}{2} \left[ n + \frac{(d-1)}{4} \right] \right\}^{2/3}$$

where d is the dimensionality of the critical point of transition of said semiconductor;

making a linear plot of said $x_n$ versus said respective photon energies; and identifying said bandgap by identifying the intercept of said linear plot of the axis corresponding to said respective photon energies.

* * * * *